April 16, 1957 C. INGRAM Plant Pat. 1,589
RUBUS PLANT
Filed Dec. 9, 1955
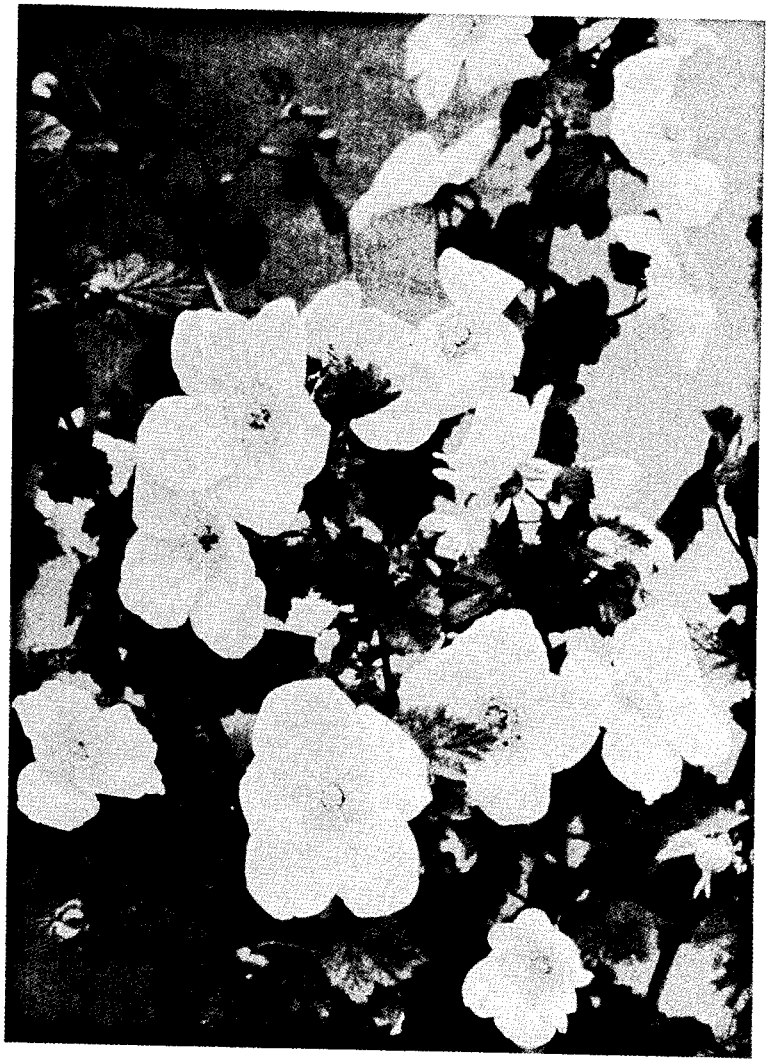
Inventor.
Collingwood Ingram
By: Robb & Robb
Attorneys.

United States Patent Office

Plant Pat. 1,589
Patented Apr. 16, 1957

1,589

RUBUS PLANT

Collingwood Ingram, Cranbrook, England, assignor to Gulf Stream Products, Inc., Wachapreague, Va., a corporation of Virginia Application December 9, 1955, Serial No. 552,245

1 Claim. (Cl. 47—60)

The present invention relates to a new and distinct variety of Rubus plant, sometimes called a flowering raspberry, which was originated by me by crossing an unnamed and unpatented seedling of *Rubus trilobus* with the variety *Rubus deliciosus* (unpatented).

Some years ago, while on an exploring expedition in central Mexico, the explorers found an unusually fine Rubus plant growing on the middle slopes of the extinct volcano "Citlaltepetl" at an altitude of about 12,000 feet. The plant was growing in the partial shade of an open woodland and was subsequently identified as *Rubus trilobus* which may be generally described as a erect shrub of from to 1½ meters in height, having woody, glabrous branches when mature, but pubescent at times when younger, cordate-ovate leaves which are angled and mostly trilobed, densely pubescent on their upper surfaces and softly villose on their under surfaces, with short, fertile branchlets, usually 1-flowered, the flowers being approximately from 5 to 8 cm. in diameter, and the sepals broadly ovate-lanceolate. The fruit of *Rubus trilobus* generally corresponds to that of *Rubus deliciosus,* but the habit differs from that of *Rubus deliciosus* in that the internodes of *Rubus triolobus* are longer on the branchlets and consequently its leaves are farther apart. *Rubus trilobus* has been found in and is native to southern Mexico and Guatemala, usually growing at an altitude of from 2800 to 3000 meters.

Following the discovery of the excellent specimens of *Rubus trilobus,* as noted above, which were brought to England, I acquired some layering materials taken from seedlings derived from seeds obtained by the explorers from the originally discovered plants of *Rubus trilobus.* The plants which I raised from the layering materials on my property in Kent, England, proved to be completely hardy, and in many respects closely resembled the variety *Rubus deliciosus* (sometimes known as "Rocky Mountain Rubus"), but differed somewhat therefrom in respect to the shape of the leaves. The pure white flowers of my plants also were larger than those of any other member of its genus of which I am aware, and were individually exceptionally attractive, but unfortunately the flowers were produced only intermittently, although over a fairly long season, and seldom, if ever, were borne in sufficient numbers at any one time to make any substantial floral display.

I thereupon undertook and endeavored to remedy this latter fault by crossing my *Rubus trilobus* plants with *Rubus deliciosus* which may be generally described as a compact, bushy grower, reaching a height of 5 feet, with large, orbicular or reniform leaves of shallowy 3 to 5-lobed form, unequally serrate and somewhat glandular. The flowers of *Rubus deliciosus* are usually borne in great profusion, are pure white in color, from 1 to 2 inches in diameter, with the blooms beginning in early summer and continuing for a long season. The berries of *Rubus deliciosus* are hemispherical, purplish or wine colored, with large, soft drupelets like those of a red raspberry. The berries are edible but are not esteemed for their eating qualities. *Rubus deliciosus* is native to the mountains of Colorado, and is found at elevations reaching as high as 8,000 feet. It is the finest of native flowering raspberries, has proved to be hardy in Massachusetts, and the flowers resemble single roses.

As the result of my crossing of *Rubus trilobus* seedlings with *Rubus deliciosus,* I was completely successful in increasing the flower productivity of the plants, and indeed, if grown in a fairly sunny position, the plants will bear on very gracefully arching boughs so many large snow-white flowers that when viewed from a short distance away, the shrub might easily be mistaken for a rose. In addition, the blooms of my new variety are beautifully shaped and are notably larger than those of *Rubus deliciosus,* and are always produced in far greater abundance. In England, my new variety normally blooms beginning with the latter half of the month of May and continuing well into the month of June.

Generally speaking, my new variety may be characterized as an improved *Rubus deliciosus,* with larger, better-shaped and more abundant flowers, and I have established that these characteristics are fixed and come true to form and are transmitted through succeeding propagations by both cuttings and layering, as performed by me on my cultivated property at Benenden, Cranbrook, Kent, England.

The accompanying drawing shows typical specimens of the vegetative growth and flowers of my new variety in different stages of development, the same being depicted in black-and-white, since the color features thereof generally correspond to those of the variety *Rubus deliciosus,* including the pure snow-white color of the flowers, and are not significant in themselves from the standpoint of distinctiveness.

The following is a detailed description of my new variety, with color terminology in accordance with general color terms of ordinary dictionary significance:

Parentage: Seedling.
- *Male parent.*—*Rubus deliciosus.*
- *Female parent.*—An unnamed seedling of *Rubus trilobus.*

Propagation: Holds its distinguishing characteristics through succeeding propagations by both cuttings and layering.

Locality where grown and observed: Benenden, Cranbrook, Kent, England.

*Plant*

Growth: Vigorous.

Root: Vigorous.

Crown: Medium size; branched.

Leaves: Large (length about 2½ inches; width about 3 inches); many; with bracts.
- *Petiole.*—Medium length (about 1¼ inches); stout.
- *Color.*—Spinach Green, Plate 0960/2 (Color Chart of the Royal Horticultural Society).

Flower stems: Short; inflorescence exposed.

Bloom: Between early and late.
- *Date of first bloom.*—Early May.
- *Date of full bloom.*—About mid-May.
- *Flowers.*—Size—approximately 2 inches or more in diameter. Color—pure white. Filaments of stamens—short (about ⅛ inch). Pollen—abundant.

Fruiting stems: Short (about ¼ inch); upright; with many branches of trusses forming attractive and gracefully arching sprays of blossoms.

Soil where grown: Loamy; well-drained.

Culture: No special culture needed.

Disease and insect resistance: No signs of any diseases or pests have been observed, as compared with other plants grown in England under the same cultural conditions.

Frost resistance: No injury from cold weather has been observed to date in England.

Drought resistance: No injury from dry weather has been observed to date in England.

Fruit: A somewhat flattened hemispherical shape; consist of a number of soft drupelets; indistinguishable from fruit of *Rubus deliciosus.*

*Color.*—Indian Lake, Plate 826/2 (Color Chart of the Royal Horticultural Society).

*Size.*—Uniform. Average length—about ¼ inch. Average breadth—about ½ inch.

*Form.*—Uniform. Apex—rounded.

Flesh: Juicy.

*Texture.*—Firm.

*Flavor.*—Sub-acid.

*Quality.*—Inferior.

I claim:

A new and distinct variety of Rubus or flowering raspberry plant, substantially as herein shown and described, characterized particularly as to novelty by its general similarity to the variety *Rubus deliciosus,* but being distinguished therefrom by its larger, better-shaped and more abundant snow-white flowers which are borne in gracefully arching sprays and resemble roses when observed from a short distance.

No references cited.